United States Patent [19]
Govindan et al.

[11] Patent Number: 6,140,531
[45] Date of Patent: Oct. 31, 2000

[54] METHOD OF PREPARING N-1-ALKENYL CARBONYLAMINO COMPOUNDS

[75] Inventors: Cheruthur Govindan, Murrysville; John M. Pascone, Harrison City, both of Pa.

[73] Assignee: PPG Industries Ohio, Inc., Cleveland, Ohio

[21] Appl. No.: 09/280,193

[22] Filed: Mar. 29, 1999

[51] Int. Cl.$^7$ .................. C07C 269/00; C07C 262/02; C07C 271/12
[52] U.S. Cl. .................. 560/163; 558/232; 558/242; 560/157; 560/162; 560/164; 560/166; 564/56; 564/57; 564/60; 564/61
[58] Field of Search .................. 558/232, 242; 560/157, 162, 163, 164, 166; 564/56, 57, 60, 61

[56] References Cited

U.S. PATENT DOCUMENTS

| | | | |
|---|---|---|---|
| 2,475,424 | 7/1949 | Dickey et al. | 260/84 |
| 2,592,254 | 4/1952 | Dickey | 260/77.5 |
| 4,089,688 | 5/1978 | Fitzgerald | 96/14 |
| 4,095,034 | 6/1978 | Mangold et al. | 560/134 |
| 4,147,716 | 4/1979 | Chung | 260/465 |
| 5,233,077 | 8/1993 | Waller | 560/157 |
| 5,606,096 | 2/1997 | Yamanaka et al. | 560/157 |
| 5,783,697 | 7/1998 | Heider et al. | 544/172 |

OTHER PUBLICATIONS

Database CAPLUS on STN, Acc. No. 1968:30729, Storck et al., 'Anion exchangers based on vinylamine.' Makromol. Chem. (1967), 110, p207–221 (abstract), 1968.
Database CAPLUS on STN, Acc. No. 1982:20522, Bechara, 'The mechanism of tin–amine synergism in the catalysis of isocyanate reaction with alcohol.' ACS Symp. Ser. (1981), 172 (Urethane Chem. Appl.), p393–402 (abstract).
Database CAPLUS on STN, Acc. No. 1968:403178, Smith, 'Effect of urethane groups on the reaction of alcohols with isocyanates.' J. Polym. Sci., Part A–1 (1968), 6(5), p1299–1306 (abstract).
M. L. Wolfrom et al, *J. Org. Chem.*, 1961, 26, 2597–2599.
L. E. Overman et al, *Tetrahedron Letters*, 1976, 36, 3089–3092.
L. E. Overman et al, *J. Org. Chem.*, 1978, 43, 2164–2167.
J. R. Pfister et al, *Synthesis*, 1983, Jan. 38–40.
T. L. Capson et al, *Tetrahedron Letters*, 1984, 25, 3515–3518.
March, J., *Advanced Organic Chemistry: Reactions, Mechanisms, and Structure*, third edition; John Wiley & Sons: New York, 1985; Chapter 8–17, p. 984.
Organic Syntheses: Collective vol. 6; John Wiley & Sons: New York, 1988; 1–N–acylamine–1,3–dienes By Curtius Rearrangement, pp. 95–101.
D. J. am Ende et al, *Organic Process Research & Development*, 1988, 2, 328–392.
Weiber et at, *J. Org. Chem.*, 1989, 54, 4659–5653.
Chemical Abstracts 13762d, 1957, N–Vinyl derivatives.

*Primary Examiner*—Johann Richter
*Assistant Examiner*—Brian J. Davis
*Attorney, Agent, or Firm*—Irwin M. Stein; James R. Franks

[57] ABSTRACT

Describes a method of producing N-1-alkenyl carbonylamino compounds represented by the following general formula I,

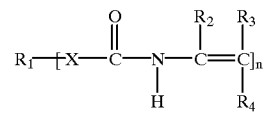

wherein $R_1$ is the residue of an active hydrogen functional material, n is a number from 1 to a number equal to the number of active hydrogen groups of said active hydrogen functional material, X is selected from O, S and $N(R_5)$, $R_5$ being hydrogen, hydrocarbyl, or $R_5$ and $R_1$ may together form a cyclic ring, $R_2$, $R_3$ and $R_4$ are each independently selected from hydrogen, $C_1$–$C_4$ alkyl and $C_2$–$C_4$ alkenyl. The method comprises the steps of: (a) heating 2-alkenoyl azide in the presence of a first inert solvent in a first reaction zone, the first inert solvent being substantially free of active hydrogen functional material; (b) transferring volatile product as it is formed in the first reaction zone of step (a) into a separate second reaction zone containing a reactive composition comprising active hydrogen functional material having active hydrogen groups selected from the group consisting of hydroxyl, thiol, primary amine, secondary amine and combinations thereof; and (c) withdrawing N-1-alkenyl carbonylamino compound from the second reaction zone.

17 Claims, No Drawings

METHOD OF PREPARING N-1-ALKENYL CARBONYLAMINO COMPOUNDS

DESCRIPTION OF THE INVENTION

The present invention relates to a method of preparing N-1-alkenyl carbonylamino compounds selected from the group consisting of N-1-alkenyl carbamate, N-1-alkenyl thiocarbamate, N-1-alkenyl urea and mixtures thereof. Particularly, the present invention relates to a method of preparing such compounds by forming a volatile product from the heating of 2-alkenoyl azide in the presence of an inert solvent, and transferring the volatile product as it is formed into a reactive composition comprising active hydrogen functional material having at least one active hydrogen group selected from hydroxyl, thiol, primary amine, secondary amine and combinations thereof. More particularly, the method of the present invention involves heating 2-alkenoyl azide in the substantial absence of active hydrogen functional material.

The use of N-1-alkenyl carbonylamino compounds, such as N-1-alkenyl carbamates, e.g., methyl N-ethenyl carbamate and tertiarybutyl N-ethenyl carbamate, as radically polymerizable monomers in the preparation of polymers and copolymers having pendent carbamate groups is known. Such polymers are described in, for example, U.S. Pat. No. 4,089,688.

N-1-alkenyl carbonylamino compounds are also useful as synthetic intermediates. For example, N-1-alkenyl carbamates are known to undergo alkylation of the carbon alpha ($\alpha$) to the nitrogen of the carbamate linkage, and are consequently useful in the preparation of, for example, beta-lactam antibiotics. See Weiber et al, *J. Org. Chem.*, 1989, 54, 4659–5653. N-1-alkenyl carbonylamino compounds, such as trans-1-N-acylamino-1,3-dienes are useful in Diels-Alder reactions as described by L. E. Overman et al, *Tetrahedran Letters*, 1976, 36, 3089–3092.

It is known that carbamates, thiocarbamates and ureas can be prepared from the reaction of isocyanates with alcohols, thiols and amines, respectively. However, due to the rapid self polymerization of 1-alkenyl isocyanates, such as vinyl isocyanate, through the alkenyl group, these materials are typically prepared in-situ from the corresponding 2-alkenoyl azide by means of the Curtius rearrangement. Carrying out the Curtius rearrangement of an acyl azide in the presence of an alcohol results in the formation of a carbamate, as described in general terms by March, J., *Advanced Organic Chemistry: Reactions, Mechanisms, and Structure,* third edition; John Wiley & Sons: New York, 1985; Chapter 8–17, page 984.

A method of preparing trans-1-N-acylamino-1,3-dienes is described by L. E. Overman et al, *J. Org. Chem.*, 1978, 43, 2164–2167. Overman et al describe preforming 1,3-dienyl isocyanate from the corresponding 2,4-dienoyl azide by the Curtius rearrangement at 110° C., followed by rapid cooling to room temperature. An alcohol, thiol or secondary amine was then added to the preformed and cooled 1,3-dienyl isocyanate to form the desired carbamate, e.g., benzyl trans-1,3-butadiene-1-carbamate, thiocarbamate or urea.

A common method of preparing benzyl N-vinyl carbamate is described by M. L. Wolfrom et al, *J. Org. Chem.*, 1961, 26, 2597–2599. In the method described by Wolfrom et al, a solution of acryloyl azide and toluene was added dropwise to a stirred and heated (110° C.) mixture of benzyl alcohol, hydroquinone and pyridine to produce benzyl N-vinyl carbamate in 60 percent over-all yield relative to the acryloyl chloride from which the acryloyl azide was prepared. Heating of acryloyl azide is thought to result in the formation of vinyl isocyanate by means of the Curtius rearrangement. It is disclose d by Wolfrom et al that the use of acryloyl azide containing trace acid, i.e., acryloyl azide that has not been purified, results in the formation of dibenzyl ethylidenedicarbamates rather than the desired benzyl N-vinyl carbamate product. In addition, Wolfrom et al disclose that attempts to isolate vinyl isocyanate resulted in the formation of an insoluble white solid, which was determined to be polyvinyl isocyanate).

It would be desirable to develop an alternative method of preparing N-1-alkenyl carbonylamino compounds that does not require the purification of 2-alkenoyl azide, is substantially free of the formation of polymeric residues, such as poly(alkenyl isocyanate) and/or poly(alkenoyl azide), and can be used on a production scale.

In accordance with the present invention, there is provided a method of producing N-1-alkenyl carbonylamino compounds represented by the following general formula I,

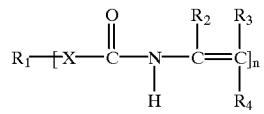

wherein $R_1$ is the residue of an active hydrogen functional material, n is a number from 1 to a number equal to the number of active hydrogen groups of said active hydrogen functional material, e.g., from 1 to 100, from 1 to 6 or from 1 to 3, X is selected from O, S and $N(R_5)$, $R_5$ being hydrogen, hydrocarbyl (e.g., $C_1$–$C_{20}$ alkyl, $C_5$–$C_8$ cycloalkyl, phenyl and benzyl), or $R_5$ and $R_1$ may together form a cyclic ring, in which case n is 1, and $R_2$, $R_3$ and $R_4$ are each independently selected from hydrogen, $C_1$–$C_4$ alkyl, e.g., methyl, ethyl, propyl, isopropyl, butyl, isobutyl and tertiary butyl, and $C_2$–$C_4$ alkenyl, e.g., ethenyl. The method of the present invention comprises the steps of:

(a) heating 2-alkenoyl azide in the presence of a first inert solvent in a first reaction zone, said first inert solvent being substantially free of active hydrogen functional material;

(b) transferring volatile product as it is formed in said first reaction zone of step (a) into a separate second reaction zone containing a reactive composition comprising active hydrogen functional material having active hydrogen groups selected from the group consisting of hydroxyl, thiol, primary amine, secondary amine and combinations thereof; and (c) withdrawing N-1-alkenyl carbonylamino compound from the second reaction zone.

Other than in the operating examples, or where otherwise indicated, all numbers expressing quantities of ingredients, reaction conditions, etc. used in the specification and claims are to be understood as modified in all instances by the term "about."

DETAILED DESCRIPTION OF THE INVENTION

When X is O, general formula I represents an N-1-alkenyl carbamate represented by the following general formula II:

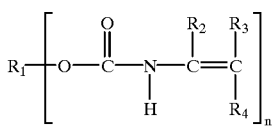

wherein $R_1$ is the residue of a hydroxyl functional material, n is a number from 1 to a number equal to the number of hydroxyl groups of the hydroxyl functional material, and $R_2$, $R_3$ and $R_4$ are as described previously herein. When X is S, general formula I represents an N-1-alkenyl thiocarbamate and $R_1$ is the residue of a thiol functional material, and when X is $N(R_5)$, general formula I represents an N-1-alkenyl urea and $R_1$ is the residue of a primary or secondary amine. In the case when n is greater than 1 and the active hydrogen functional material of which $R_1$ is a residue has different active hydrogen groups, e.g., hydroxyl and thiol groups, general formula I represents an N-1-alkenyl carbonylamino compound having combinations of N-1-alkenyl carbamate, N-1-alkenyl thiocarbamate and N-1-alkenyl urea groups. In a preferred embodiment of the present invention, $R_1$ is the residue of a hydroxyl functional material, X is O, n is 1, at least one of $R_2$, $R_3$ and $R_4$ is hydrogen, and more preferably each of $R_2$, $R_3$ and $R_4$ is hydrogen.

The 2-alkenoyl azide of the method of the present invention may be represented by the following general formula III:

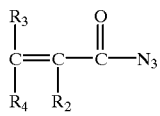

wherein $R_2$, $R_3$ and $R_4$ are as described previously herein. The 2-alkenoyl azide is prepared in accordance with known methods, e.g., from the reaction of 2-alkenoyl chloride and sodium azide, optionally in the presence of a phase transfer catalyst. A general method of preparing acyl azides under phase transfer conditions is described by J. R. Pfister et al, *Synthesis*, 1983, January, 38–40. When each of $R_2$, $R_3$ and $R_4$ are hydrogen, general formula III represents propenoyl azide, more commonly referred to as acryloyl azide.

While not intending to be bound by any theory, it is believed based on the evidence at hand that heating 2-alkenoyl azide in the method of the present invention results in the formation of 1-alkenyl isocyanate, which may be represented by the following general formula IV:

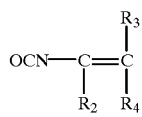

wherein $R_2$, $R_3$ and $R_4$ are as described previously herein. When each of $R_2$, $R_3$ and $R_4$ are hydrogen, general formula IV represents ethenyl isocyanate, more commonly referred to as vinyl isocyanate. It is believed that the transformation of 2-alkenoyl azide into 1-alkenyl isocyanate occurs by means of the Curtius rearrangement, as represented by the following general scheme A.

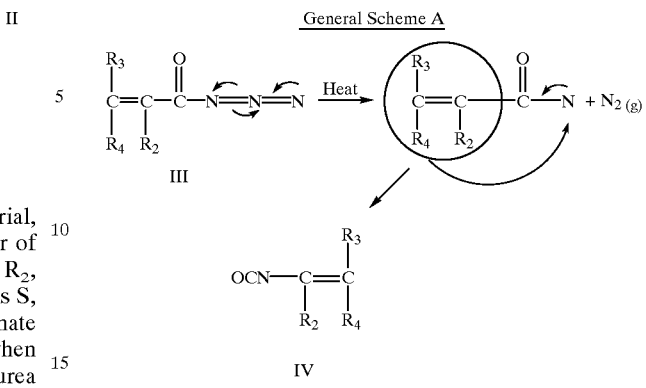

In general scheme A, the arcuate arrows represent the intramolecular movement of either electron pairs or moieties. Occurrence of the Curtius rearrangement is evidenced by the observed co-product formation of nitrogen gas while heating 2-alkenoyl azide in the method of the present invention. Additionally, detection of 1-alkenyl isocyanate by analytical methods, e.g., infrared spectroscopy, provides further evidence for the occurrence of the Curtius rearrangement in the method of the present invention.

In the method of the present invention, 2-alkenoyl azide is heated in the presence of the first inert solvent to a temperature at least sufficient to result in the formation of a volatile product, which is believed to be 1-alkenyl isocyanate as discussed previously herein. Typically, this temperature is in the range of from 60° C. to 150° C., preferably from 80° C. to 120° C. and more preferably from 100° C. to 115° C., inclusive of the recited values. Heating of the 2-alkenoyl azide in the presence of the first inert solvent is typically performed under conditions of ambient pressure, but may alternatively be done under lesser or greater pressures.

As the volatile product is formed in the first reaction zone, it is transferred continuously into the second reaction zone in the method of the present invention. The volatile product is typically transferred either alone or in combination with the first inert solvent by means of distillation and/or vapor transfer. Correspondingly, the volatile product and optionally the first inert solvent are transferred into the second reaction zone in a physical form selected from distillate, vapor and a combination thereof. Vapor transfer can be achieved by known methods, including, for example, the use of an absorption column or tower in which the reactive composition comprising active hydrogen functional material is circulated, and into which the volatile product and optionally the first inert solvent vapor are transferred.

The first inert solvent may be selected from any solvent or combination of solvents that has a boiling point at least equal to the temperature at which the volatile product is formed from 2-alkenoyl azide, and in which the 2-alkenoyl azide and distillate of the volatile product are both soluble. In the present invention, when the volatile product formed in the first reaction zone is transferred alone as distillate and/or vapor into the second reaction zone, the first inert solvent also preferably has a boiling point greater than that of the volatile product.

As used herein and in the claims, by "inert solvent" is meant a solvent that will neither react with nor form covalent bonds with either the 2-alkenoyl azide or the volatile product formed in the first reaction zone. The first inert solvent is preferably an organic solvent. Classes of organic solvents useful in the method of the present invention include, but are not limited to, esters of carboxylic acids, ethers, e.g., methyl tertiarybutyl ether, cyclic ethers, e.g., 1,3-dioxane, 1,4-dioxane and 1,3-dioxepane, $C_5$–$C_{10}$ alkanes, $C_5$–$C_8$ cycloalkanes, aromatic hydrocarbon solvents, e.g., toluene and xylene, halogenated hydrocarbon solvents, e.g., 1-bromo-2-chloroethane, 1,2-dichloroethane and 1,2-dibromoethane, amides, nitrites, sulfoxides, sulfones and mixtures thereof. In a preferred embodiment of the present invention, the first inert solvent is selected from one or more aromatic hydrocarbon solvents, e.g., toluene and xylene.

As used herein and in the claims, by "substantially free of active hydrogen functional material" is meant that the active hydrogen functional material is present in an amount less than, for example, 0.5 percent by weight and preferably less than 0.1 percent by weight, based on total weight. In the method of the present invention, other than in the reactive composition in the second reaction zone, there is preferably no active hydrogen functional material present.

The volatile product formed in the first reaction zone is continuously transferred in the method of the present invention into the second reaction zone, which contains a reactive composition comprising active hydrogen functional material. Active hydrogen functional materials useful in the method of the present invention include, for example: materials having a single active hydrogen functional group, e.g., monofunctional alcohols, thiols and amines; materials having two or more active hydrogen functional groups, e.g., polyols, polythiols, polyamines, and materials containing combinations of hydroxyl, thiol and amine groups; and oligomers and polymers having at least one active hydrogen group.

Examples of active hydrogen functional materials having a single hydroxyl group, that may be used in the present invention include, but are not limited to: $C_1$–$C_{20}$ linear or branched alcohols, e.g., methanol, ethanol, propanol, isopropanol, butanol, tertiary butanol, pentanol, isopentanol, hexanol, heptanol, octanol, nonanol, decanol, dodecanol, pentadecanol, octadecanol and eicosanol; hydroxy functional ethers of alkylene glycols, e.g., butyl 2-hydroxyethyl ether, hexyl 2-hydroxyethyl ether, methyl 2-hydroxypropyl ether and phenyl 2-hydroxypropyl ether; hydroxy functional esters of carboxylic acids, e.g., 2-hydroxyethyl methacrylate and 2-hydroxyethyl acetate; cycloalkyl alcohols having from 1 to 12 carbons in the cyclic ring, e.g., cyclopropanol, cyclobutanol, cyclopentanol, cyclohexanol, cycloheptanol, norborneol, 2-norbornanemethanol, cyclooctanol and cyclododecanol; and alcohols containing aromatic rings, e.g., phenol, ortho-, meta- and para-methyl phenol, nonyl phenol, benzyl alcohol, benzyloxyphenol, benzyloxypropanol, 4-hydroxydiphenylmethane and naphthol.

Non-limiting examples of polyols from which the active hydrogen functional material of the present invention may be selected include: alkylene glycols, e.g., ethylene glycol and propylene glycol, 4,4'-isopropylidenediphenol, trimethylol ethane, trimethylol propane, trishydroxyethyl isocyanurate and pentaerythritol.

Mono and polyfunctional thiols from which the active hydrogen functional material of the present invention may be selected include thiol functional materials corresponding to those alcohols and polyols recited previously herein, e.g., methylthiol, tertiary butylthiol, benzylthiol and 1,2-ethylene dithiol.

Primary and secondary amines from which the active hydrogen functional material of the present invention may be selected, include, but are not limited to, amines having one or two substituents selected from $C_1$–$C_{20}$ alkyl, e.g., methylamine and diethylamine, $C_5$–$C_8$ cycloalkyl, e.g., cyclohexyl amine, phenyl, $C_1$–$C_9$ alkyl substituted phenyl, benzyl, $C_1$–$C_9$ alkyl substituted benzyl and combinations thereof. Cyclic amines including, for example, piperidine, and heterocyclic amines including, for example, 1H-azoles, such as 1H-imidazole, 1H-pyrazole, 3,5-dimethyl-1H-pyrazole, 1H-1,2,3-triazole, 1H-1,2,3-benzotriazole, 1H-1,2,4-triazole, 1H-5-methyl-1,2,4-triazole and 1H-3-amino-1,2,4-triazole. Polyfunctional amines having two or more amine groups, that may be used in the method of the present invention include, but are not limited to, alkyleneamines, e.g., ethylenediamine, diethylenetriamine, triethylenetetramine, piperazine, N,N-dimethylethylenediamine and 1,2-propylenediamine.

Active hydrogen functional materials having two or more active hydrogen groups selected from combinations of hydroxyl, thiol and amine groups, that may be used in the present invention include, for example, mono- and di(2-hydroxyethyl)amine, mono- and di(2-mercaptoethyl)amine, 2-mercaptoethanol, 3-mercapto-1,2-propanediol, 4-mercaptophenol and 2,4-dimercaptophenol. Examples of oligomers and polymers having one or more active hydrogen groups from which the active hydrogen functional material of the present invention may be selected include, but are not limited to, active hydrogen functional polyesters, polyethers, polyurethanes and poly(meth)acrylates. As used herein, the term "(meth)acrylate" is intended to refer to methacrylates, acrylates and combinations of methacrylates and acrylates.

The ratio of the total molar equivalents of active hydrogen groups present in the reactive composition of the second reaction zone to the total molar equivalents of 2-alkenoyl azide heated in the first reaction zone, is typically at least 1:1, and may range from 1:1 to 5:1, e.g., from 1:1 to 2:1. While the scope of the present invention is inclusive of molar equivalent ratios of active hydrogen groups to 2-alkenoyl azide that are less than 1:1, the use of such ratios can result in the formation of unwanted co-products, such as poly(alkenyl isocyanate).

With reference to general formula I, when the active hydrogen functional material of the separate reactive composition is benzyl alcohol, X is O, $R_1$ is the benzyl radical and n is 1. With further reference to general formula I and when the active hydrogen functional material is trimethylol propane, n is 3, X is O, and $R_1$ is the 1,1,1-trimethylene propyl radical. In a preferred embodiment of the present invention, the active hydrogen function material is a monofunctional alcohol, e.g., benzyl alcohol, X is O, and n is 1 in general formula I.

The reactive composition in the second reaction zone of the method of the present invention may optionally include a free radical polymerization inhibitor. The free radical polymerization inhibitor may be selected from any of those which inhibit the formation of, for example, poly(alkenyl isocyanate). Non-limiting examples of free radical polymerization inhibitors that may be used in the present invention include, hydroquinone, hydroquinone monomethyl ether, phenothiazine and hindered phenols, e.g., 2,6-di-tert-butyl-4-methylphenol. A preferred free radical polymerization inhibitor in the present invention is phenothiazine. The first inert solvent may also contain free radical polymerization inhibitor. The free radical polymerization inhibitor is typically present in the reactive composition in the second reaction zone and optionally in the first inert solvent in the first reaction zone in an inhibiting amount, e.g., from 0.01 percent to 0.5 percent by weight, based on total weight, e.g., the total initial weight of the reactive composition.

In the method of the present invention, the contents of the reactive composition in the second reaction zone are preferably maintained at a temperature that is less than the temperature at which the 2-alkenoyl azide is heated to in the first reaction zone. The temperature of the contents of the reactive composition in the second reaction zone is typically at least 0° C., and less than 50° C., preferably less than 25° C. and more preferably less than 10° C. The temperature of the contents of the reactive composition in the second reaction zone may range between any combination of these values, inclusive of the recited values.

The reactive composition in the second reaction zone of the present invention may also comprise an inert solvent. This inert solvent, e.g., a second inert solvent, includes those solvents in which each of the active hydrogen functional material, the volatile product transferred from the first reaction zone, and optionally the N-1-alkenyl carbonylamino compound are soluble. The second inert solvent may be selected from those solvents described with respect to the first inert solvent. If present, the second inert solvent is typically present in an amount of from 5 percent to 70 percent by weight, e.g., from 10 percent to 50 percent by weight, based on the total initial weight of the reactive composition in the second reaction zone. The second inert solvent is preferably the same as the first inert solvent.

A catalyst for catalyzing the reaction between the active hydrogen functional material and the volatile product transferred from the first reaction zone may optionally be present in the reactive composition in the second reaction zone. Examples of suitable catalysts useful in the present invention, include, but are not limited to, metal compounds, in particular, organic tin compounds, e.g., tin(II) octanoate and dibutyltin(IV) dilaurate, tertiary amines, e.g., diazabicyclo[2.2.2]octane, triethyl amine and tributyl amine, and combinations of organic tin compounds and tertiary amines. The catalyst if used, is typically present in a catalytic amount, e.g., from 0.05 percent to 1.0 percent by weight, based on the initial weight of the reactive composition in the second reaction zone. In a preferred embodiment of the present invention, the catalyst is a tertiary amine, e.g., triethylamine.

In an embodiment of the present invention, 2-alkenoyl azide is added continuously to the first inert solvent, which has been preheated in the first reaction zone to a temperature at least sufficient to result in the formation of the volatile product. The temperature to which the first inert solvent is preheated in the first reaction zone is typically from 60° C. to 150° C., preferably from 80° C. to 120° C. and more preferably from 100° C. to 115° C., inclusive of the recited values. The 2-alkenoyl azide is typically added as a solution of 2-alkenoyl azide in an inert solvent, e.g., a third inert solvent. This third inert solvent may be selected from those solvents described with respect to the first inert solvent, and is preferably the same as the first inert solvent. The 2-alkenoyl azide added to the first inert solvent is substantially free of active hydrogen functional material, and is also preferably maintained at a temperature less than the temperature to which the first inert solvent is preheated, e.g., from 0° C. to 25° C. The 2-alkenoyl azide solution (added to the preheated first inert solvent) may also contain an inhibiting amount of free radical polymerization inhibitor selected from those as previously recited herein.

The method of the present invention further comprises withdrawing N-1-alkenyl carbonylamino compound from the second reaction zone. Depending on the contents of the reactive composition in the second reaction zone, the N-1-alkenyl carbonylamino compound may be withdrawn alone or along with other materials present therein, e.g., inert solvent, unreacted active hydrogen functional material, polymerization inhibitor, catalyst and mixtures of these materials. Typically, the N-1-alkenyl carbonylamino compound is withdrawn from the second reaction zone along with other materials present in the reactive composition.

The method of the present invention optionally comprises isolating N-1-alkenyl carbonylamino compound withdrawn from the second reaction zone. Suitable methods of isolation include those known in the art, for example, crystallization, solvent evaporation and distillation.

The present invention is more particularly described in the following examples, which are intended to be illustrative only, since numerous modifications and variations therein will be apparent to those skilled in the art. Unless otherwise specified, all parts and percentages are by weight.

The preparation of benzyl N-vinyl carbamate according to the method of the present invention is described in the following examples. The acryloyl azide used in the examples described herein was prepared from the reaction of acryloyl chloride and sodium azide as described below.

Preparation of Acryloyl Azide

| Ingredients | Amount |
|---|---|
| Charge 1 | |
| sodium azide | 69 grams |
| distilled water | 200 ml |
| Charge 2 | |
| phase transfer catalyst (a) | 0.09 grams |
| toluene | 200 ml |
| Charge 3 | |
| acryloyl chloride | 90 grams |
| Charge 4 | |
| pyridine | 0.3 grams |

(a) Adogen ® 464 quaternary ammonium salt [CAS No. 63393-96-4] obtained commercially from Aldrich Chemical Company, which describes it as methyl-trialkyl ($C_8$–$C_{10}$) ammonium chloride.

Charge 1 was added to a 1 liter triple necked round bottom flask equipped with mechanical stir blade and thermometer. The contents of the flask were stirred under ambient conditions to ensure that the sodium azide was dissolved in the water. With continued agitation, Charge 2 was added to the flask, and the contents were cooled to a temperature of 5° C. Charge 3 was next added over a period of 90 minutes while maintaining the stirred contents of the flask at a temperature of between 0° C. and 5° C. Upon completing the addition of Charge 3, the contents of the flask were stirred for an additional 45 minutes at a temperature of between 0° C. and 5° C. The contents of the flask were then transferred to a separatory funnel. After standing for an amount of time sufficient to allow phase separation, the aqueous phase was discarded and 267.2 grams of organic phase were retained. Charge 4 was added to the retained organic phase.

Preparation of Benzyl N-vinyl Carbamate

A 1 liter triple necked round bottom flask equipped with a mechanical stir blade, a heating mantle and thermometer coupled together through a temperature feed-back control device, and a distillation assembly having a receiving flask was used to prepare benzyl N-vinyl carbamate according to the method of the present invention. To the receiving flask, i.e., the second reaction zone, of the distillation assembly was added 86 grams of benzyl alcohol, 0.1 grams of triethylamine and 0.04 grams of phenothiazine, which were cooled to and maintained at a temperature of between 0° C. and 10° C. with constant stirring using a magnetic stir bar. To the 1 liter flask, i.e., the first reaction zone, was added 200 ml of toluene and 0.5 grams of phenothiazine, which were then heated under continuous agitation to a temperature of 107° C.

With continued agitation, 267 grams of the organic phase obtained from the preparation of the acryloyl azide, as described above, was added slowly to the 1 liter flask over a period of 4 hours. During the course of this addition, volatile product and a portion of the toluene solvent were continuously removed from the first reaction zone in the form of vapors, which were condensed in the distillation column and transferred into the second reaction zone as distillate. Sufficient heat was applied by means of the heating mantle to maintain the contents of the 1 liter flask at a temperature of 105° C. during the course of this four hour addition. The head temperature of the distillation apparatus was observed to range between 89° C. and 91° C. throughout most of the four hour addition.

With the completion of the addition of the acryloyl azide organic phase, 10 ml of toluene were flushed through the addition lines into the 1 liter flask. After an ensuing period of approximately 18 minutes the temperature of the contents of the 1 liter flask were observed to rise to 110° C., at which point the heating mantle was dropped and the distillation stopped. The contents of the receiving flask weighed 279.1 grams. A significant amount of polymer residue was not observed to form in either the condenser or the receiving flask during the preparation of the benzyl N-vinyl carbamate.

After stirring overnight at room temperature, the contents of the receiving flask were analyzed by high pressure liquid chromatography (HPLC) and determined to have the following composition: 0.68 percent benzyl alcohol, 0.98 percent acryloyl azide, 67 percent benzyl N-vinyl carbamate, and 31 percent toluene (percents being based on total peak area).

Isolation of Benzyl N-vinyl Carbamate

The contents of the receiving flask were next stripped on a roto-evaporator to a residue weight of 185 grams. To this residue was added 380 ml of heptane. With stirring at 25OC, a small amount of seed crystals of benzyl N-vinyl carbamate (less than 0.5 grams) were added to the residue/heptane mixture. With continued stirring, the mixture was cooled to and held at a temperature of 5° C. for one hour, during which crystals were observed to form. The crystals were collected by filtration, washed with additional heptane, and air dried. A total of 128 grams of dried crystals were collected and found to have a melting point of from 41° C. to 44° C. (as determined using a Thomas Hoover capillary melting point apparatus) and a purity of 96.7 percent by weight (as determined by HPLC analysis). Based on the results of the melting point analysis, the crystals were determined to be crystals of benzyl N-vinyl carbamate.

The above example shows that the method of the present invention results in the production of an N-1-alkenyl carbonylamino compound, such as benzyl N-vinyl carbamate, in both high yield and purity. In the above described "Preparation of Benzyl N-vinyl Carbamate" section, a significant amount of polymer residue was not observed to form in either the condenser or the receiving flask of the distillation apparatus.

In the above described "Preparation of Benzyl N-vinyl Carbamate" section, an N-vinyl thiocarbamate, such as benzyl N-vinyl thiocarbamate, or an N-vinyl urea, such as N-benzyl N'-vinyl urea, can be produced by substituting a thiol, e.g., benzyl mercaptan, or amine, e.g., benzyl amine, for the benzyl alcohol.

The present invention has been described with reference to specific details of particular embodiments thereof. It is not intended that such details be regarded as limitations upon the scope of the invention except insofar as and to the extent that they are included in the accompanying claims.

We claim:

1. A method of producing N-1-alkenyl carbonylamino compounds represented by the following general formula,

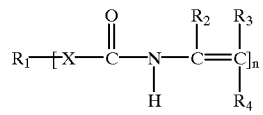

wherein $R_1$ is the residue of an active hydrogen functional material, n is a number from 1 to a number equal to the number of active hydrogen groups of said active hydrogen functional material, X is selected from O, S and $N(R_5)$, $R_5$ being hydrogen, hydrocarbyl, or $R_5$ and $R_1$ together form a cyclic ring, $R_2$, $R_3$ and $R_4$ are each independently selected from hydrogen, $C_1$–$C_4$ alkyl and $C_2$–$C_4$ alkenyl, said method comprising the steps of:

(a) heating 2-alkenoyl azide in the presence of a first inert solvent in a first reaction zone, said first inert solvent being substantially free of active hydrogen functional material;

(b) transferring volatile product as it is formed in said first reaction zone of step (a) along with a portion of said first inert solvent into a separate second reaction zone containing a reactive composition comprising active hydrogen functional material having active hydrogen groups selected from the group consisting of hydroxyl, thiol, primary amine, secondary amine and combinations thereof; and (c) withdrawing N-1-alkenyl carbonylamino compound from the second reaction zone.

2. The method of claim 1 wherein each of the volatile product formed in said first reaction zone and said portion of said first inert solvent are transferred in step (b) in a physical form selected from vapor, distillate and a combination thereof.

3. The method of claim 1 wherein 2-alkenoyl azide is added continuously to said first inert solvent.

4. The method of claim 1 wherein the contents of said reactive composition in the second reaction zone are maintained at a temperature less than the temperature to which 2-alkenoyl azide is heated in the presence of said first inert solvent in said first reaction zone.

5. The method of claim 1 wherein said reactive composition in the second reaction zone further comprises a free radical polymerization inhibitor selected from the group consisting of phenothiazine, hydroquinone, hydroquinone monoalkyl ether, hindered phenols and mixtures thereof.

6. The method of claim 1 wherein said reactive composition in the second reaction zone further comprises a catalyst selected from the group consisting of organic tin compounds, tertiary amines and mixtures thereof.

7. The method of claim 1 wherein said reactive composition in the second reaction zone further comprises a second inert solvent, said first and second inert solvents being each independently selected from the group consisting of esters of carboxylic acids, ethers, cyclic ethers, $C_5$–$C_{10}$ alkanes, $C_5$–$C_8$ cycloalkanes, aromatic hydrocarbon solvents, halogenated hydrocarbon solvents, amides, nitriles, sulfoxides, sulfones and mixtures thereof.

8. The method of claim 1 wherein the active hydrogen functional material is a hydroxyl functional material, $R_1$ is the residue of said hydroxyl functional material, and X is O.

9. The method of claim 8 wherein said hydroxyl functional material is selected from the group consisting of methanol, ethanol, propanol, isopropanol, butanol, isobutyl alcohol, tertiary butyl alcohol, ethylene glycol, trimethylol propane, pentaerythritol, phenol, benzyl alcohol and mixtures thereof.

10. The method of claim 9 wherein the 2-alkenoyl azide is acryloyl azide, and $R_2$, $R_3$ and $R_4$ are each hydrogen.

11. The method of claim 1 further comprising isolating N-1-alkenyl carbonylamino compound withdrawn from the second reaction zone.

12. A method of producing N-1-alkenyl carbamates represented by the following general formula,

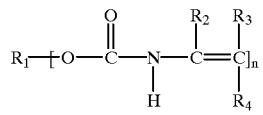

wherein $R_1$ is the residue of a hydroxyl functional material, n is a number from 1 to a number equal to the number of hydroxyl groups of said hydroxyl functional material, and $R_2$, $R_3$ and $R_4$ are each independently selected from hydrogen, $C_1$–$C_4$ alkyl and $C_2$–$C_4$ alkenyl, said method comprising the steps of:

(a) heating a first inert solvent in a first reaction zone, said first inert solvent being substantially free of hydroxyl functional material;

(b) adding continuously 2-alkenoyl azide to said first inert solvent in said first reaction zone;

(c) transferring volatile product as it is formed in said first reaction zone along with a portion of said first inert solvent into a separate second reaction zone containing a reactive composition comprising hydroxyl functional material; and (d) withdrawing N-1-alkenyl carbamate from the second reaction zone.

13. The method of claim 12 wherein each of the volatile product formed in said first reaction zone and said portion of said first inert solvent are transferred in step (c) in a physical form selected from vapor, distillate and a combination thereof.

14. The method of claim 13 wherein said reactive composition in the second reaction zone further comprises a free radical polymerization inhibitor selected from the group consisting of phenothiazine, hydroquinone, hydroquinone monoalkyl ether, hindered phenols and mixtures thereof, and a catalyst selected from the group consisting of organic tin compounds, tertiary amines and mixtures thereof.

15. The method of claim 14 wherein said hydroxyl functional material is selected from the group consisting of methanol, ethanol, propanol, isopropanol, butanol, isobutyl alcohol, tertiary butyl alcohol, ethylene glycol, trimethylol propane, pentaerythritol, phenol, benzyl alcohol and mixtures thereof.

16. The method of claim 15 wherein the 2-alkenoyl azide is acryloyl azide, and $R_2$, $R_3$ and $R_4$ are each hydrogen.

17. The method of claim 16 wherein said hydroxyl functional material is benzyl alcohol, $R_1$ is the benzyl radical, and n is 1.

* * * * *